(12) United States Patent
Chelak

(10) Patent No.: US 8,696,598 B2
(45) Date of Patent: Apr. 15, 2014

(54) PHLEBOTOMY DEVICE HAVING TEMPERATURE SENSOR FOR DETECTING FLASHBACK

(75) Inventor: Todd M. Chelak, Westborough, MA (US)

(73) Assignee: Covidien LP, Mansfield, MA (US)

( * ) Notice: Subject to any disclaimer, the term of this patent is extended or adjusted under 35 U.S.C. 154(b) by 349 days.

(21) Appl. No.: 13/077,167

(22) Filed: Mar. 31, 2011

(65) Prior Publication Data

US 2011/0178426 A1 Jul. 21, 2011

Related U.S. Application Data

(62) Division of application No. 12/212,184, filed on Sep. 17, 2008, now Pat. No. 7,918,805.

(60) Provisional application No. 60/995,588, filed on Sep. 27, 2007.

(51) Int. Cl.
*A61B 5/00* (2006.01)
*B65D 81/00* (2006.01)
*A61M 5/178* (2006.01)
*A61B 19/00* (2006.01)

(52) U.S. Cl.
USPC ...... 600/584; 600/549; 600/573; 604/168.01; 604/404

(58) Field of Classification Search
USPC .......... 600/549, 573, 583, 584; 604/118, 122, 604/168.01, 404, 412, 413
See application file for complete search history.

(56) References Cited

U.S. PATENT DOCUMENTS

| | | | |
|---|---|---|---|
| 3,886,930 | A | 6/1975 | Ryan |
| 3,916,892 | A | 11/1975 | Latham, Jr. |
| 4,106,497 | A | 8/1978 | Percarpio |
| 4,280,496 | A | 7/1981 | Van Baelen |
| 4,365,630 | A | 12/1982 | McFarlane |
| 4,416,290 | A | 11/1983 | Lutkowski |
| 4,788,986 | A | 12/1988 | Harris |
| 4,904,242 | A | 2/1990 | Kulli |
| 4,947,863 | A | 8/1990 | Haber et al. |
| 4,971,068 | A | 11/1990 | Sahi |

(Continued)

FOREIGN PATENT DOCUMENTS

| | | |
|---|---|---|
| DE | 4011440 A1 | 10/1991 |
| EP | 0619096 A1 | 10/1994 |

(Continued)

OTHER PUBLICATIONS

European Search Report regarding related application serial No. EP 08164907.1 dated Jan. 4, 2010, 9 pgs.

(Continued)

*Primary Examiner* — Sean Dougherty
*Assistant Examiner* — Devin Henson
(74) *Attorney, Agent, or Firm* — Lisa E. Winsor, Esq.

(57) ABSTRACT

A phlebotomy device includes a needle defining a lumen and having a proximal end portion and a distal end portion. The distal end portion includes a sharpened tip configured to pierce tissue. The phlebotomy device further includes a sensor disposed at least partially within the lumen. The sensor has a first state and a second state and is configured to transition from the first state to the second state upon exposure to blood at physiological temperature.

8 Claims, 2 Drawing Sheets

(56) References Cited

U.S. PATENT DOCUMENTS

| | | | |
|---|---|---|---|
| 5,030,207 | A | 7/1991 | Mersch et al. |
| 5,032,116 | A | 7/1991 | Peterson et al. |
| 5,178,157 | A | 1/1993 | Fanlo |
| 5,303,713 | A | 4/1994 | Kurose |
| 5,314,410 | A | 5/1994 | Marks |
| 5,401,250 | A | 3/1995 | Shields |
| 5,450,856 | A | 9/1995 | Norris |
| 5,613,500 | A | 3/1997 | Bishop |
| 5,782,820 | A | 7/1998 | Roland |
| 6,063,040 | A | 5/2000 | Owen et al. |
| 6,551,288 | B2 | 4/2003 | Payne et al. |
| 6,905,483 | B2 | 6/2005 | Newby et al. |
| 7,014,623 | B2 * | 3/2006 | Prestidge et al. ............ 604/110 |
| 7,160,267 | B2 | 1/2007 | Brown |
| 7,267,653 | B2 | 9/2007 | Higaki et al. |
| 7,918,805 | B2 | 4/2011 | Chelak |
| 2005/0283093 | A1 | 12/2005 | Conway et al. |
| 2008/0319346 | A1 | 12/2008 | Crawford et al. |
| 2011/0184316 | A1 | 7/2011 | Chelak |

FOREIGN PATENT DOCUMENTS

| | | |
|---|---|---|
| EP | 1016428 A | 7/2000 |
| JP | 2000166903 A | 6/2000 |
| WO | 03043496 A2 | 5/2003 |

OTHER PUBLICATIONS

Office action issued Jul. 1, 2010 in related U.S. Appl. No. 12/212,184, 12 pgs.

Response filed Oct. 1, 2010 to Office Action dated Jul. 1, 2010 from related U.S. Appl. No. 12/212,184, 13 pgs.

Office action issued May 15, 2012 in related U.S. Appl. No. 13/077,179, 10 pgs.

Response filed Jul. 19, 2012 to Office Action issued May 15, 2012 in related U.S. Appl. No. 13/077,179, 8 pgs.

Office action issued Sep. 20, 2012 in related U.S. Appl. No. 13/077,179, 13 pgs.

* cited by examiner

PHLEBOTOMY DEVICE HAVING TEMPERATURE SENSOR FOR DETECTING FLASHBACK

CROSS-REFERENCE TO RELATED APPLICATION

The present application is a divisional application of U.S. patent application Ser. No. 12/212,184 filed Sep. 17, 2008, which claimed priority to U.S. Patent Application 60/995,588, filed on Sep. 27, 2007, both of which are incorporated by reference in their respective entireties.

BACKGROUND

The present disclosure relates to medical needles. More particularly, the present disclosure relates to phlebotomy needles with a flashback sensor.

Phlebotomy is the process of removing blood for a variety of medical and scientific purposes. This process entails the penetration of a human vein by a medical device containing a hollow needle to draw blood. Phlebotomy is an invasive procedure and, when conducted improperly, may lead to infection or physical trauma at the penetration site, or it may simply fail to yield a sufficient quantity of blood. Therefore, healthcare personnel, including medical students, nurses, and healthcare technicians, require training to properly use a medical device during a phlebotomy.

The state of the art contains numerous examples of medical devices adapted to draw blood from patients. These devices include standard needle-syringes, butterfly needle sets, and phlebotomy needles. Typically, a butterfly needle set includes a hollow needle having a sharpened distal end and a proximal end. The proximal end of the hollow needle is secured to a needle hub. In turn, a proximal portion of the needle hub is connected to flexible tubing. The needle hub defines a fluid conduit communicating with the tubing and includes a pair of flexible, radially extending wings that facilitate grasping of the butterfly needle set by medical personnel. Generally, the flexible tubing is formed of a transparent material that allows medical personnel to visualize blood flow, i.e., flashback, through the tubing immediately proximal to the needle hub. Visualization of flashback permits medical personnel to confirm that the needle has been properly inserted into a patient.

Generally, phlebotomy needles do not include structures for sensing or visualizing flashback. Although the lack of a structure for visualizing flashback in phlebotomy needles is not a major drawback for more experienced medical personnel, for those having little experience drawing blood with phlebotomy needles, the lack of any means to confirm that the needle has been properly positioned within a patient may increase the time required to draw blood and add to the discomfort of the patient.

In an attempt to overcome the above disadvantages, U.S. Pat. No. 5,450,856 to Norris discloses a phlebotomy needle attached to a blood collection tube. This phlebotomy needle includes an outboard needle, an inboard needle and a bulb therebetween. The bulb is clear and allows medical personnel to visualize blood within the bulb when the outboard needle has been properly positioned within the vein of a patient. The bulb also includes a button that can be depressed by medical personnel to vent air from within the needle. Air within the needle prevents blood from flowing through the needle and must be vented.

U.S. Patent Application 60/877,937 by Weilbacher et al. ("Weilbacher"), filed on Dec. 29, 2006, also discloses a phlebotomy needle including a structure that permits visualization of flashback. This phlebotomy needle includes a distal needle portion, a proximal needle portion and a central needle portion. The central needle portion defines an opening and a fluid channel in communication with the opening. The phlebotomy needle additionally includes a material positioned adjacent to the opening. This material allows passage of air through the opening to exit the fluid channel while preventing passage of blood. In addition, the material enables visualization of blood flow.

Although the Norris and Weilbacher phlebotomy needles facilitate visualization of flashback, a need exists for other apparatus and methods for sensing flashback during phlebotomy.

SUMMARY

The present invention relates to a phlebotomy device including a needle defining a lumen and having a proximal end portion and a distal end portion. The distal end portion includes a sharpened tip configured to pierce tissue. The phlebotomy device further includes a sensor disposed at least partially within the lumen. The sensor has a first state and a second state, and is configured to transition from the first state to the second state upon exposure to blood at physiological temperature.

In one embodiment, the sensor is made of shape memory alloy.

In one embodiment, the sensor is made of nickel-titanium alloy.

In one embodiment, the sensor is a wire.

In one embodiment, the sensor has a proximal end portion and a distal end portion having a generally helical shape.

In one embodiment, the sensor has a proximal end and a distal end fixed within the lumen of the needle.

In one embodiment, the phlebotomy device further includes a needle holder supporting the needle.

In one embodiment, the needle holder defines a cavity, wherein the distal end portion of the needle extends outwardly from the cavity and the proximal end portion of the needle is supported within the cavity.

In one embodiment, the phlebotomy device further includes a deformable valve positioned about the proximal end portion of the needle.

In one embodiment, the deformable valve includes a tubular section, an indicator, and a weakened wall section connecting the tubular section and the indicator.

In one embodiment, the indicator is made of an elastomeric material.

In one embodiment, the deformable valve is configured to move between a first collapsed position to a second extended position upon transition of the sensor from the first state to the second state.

In one embodiment, the sensor extends proximally when transitioning from the first state to the second state.

In one embodiment, the sensor contacts the deformable valve to move the deformable valve from the first collapsed position to the second extended position as the sensor transitions from a first state to the second state.

In an alternate embodiment, the phlebotomy device includes a needle having a distal needle portion and defining a lumen extending therethrough a sensor disposed within the lumen, the sensor being fixed to the distal needle portion and having a non-linear portion. The non-linear portion of the sensor transitions to a substantially linear state when in contact with blood at physiological temperature.

In one embodiment, the non-linear portion has a sinusoidal configuration.

In one embodiment, the non-linear portion has a helical configuration.

BRIEF DESCRIPTION OF THE DRAWINGS

Various embodiments of the presently disclosed phlebotomy device are described herein with reference to the drawings.

DETAILED DESCRIPTION OF THE DRAWINGS

Figure 1:
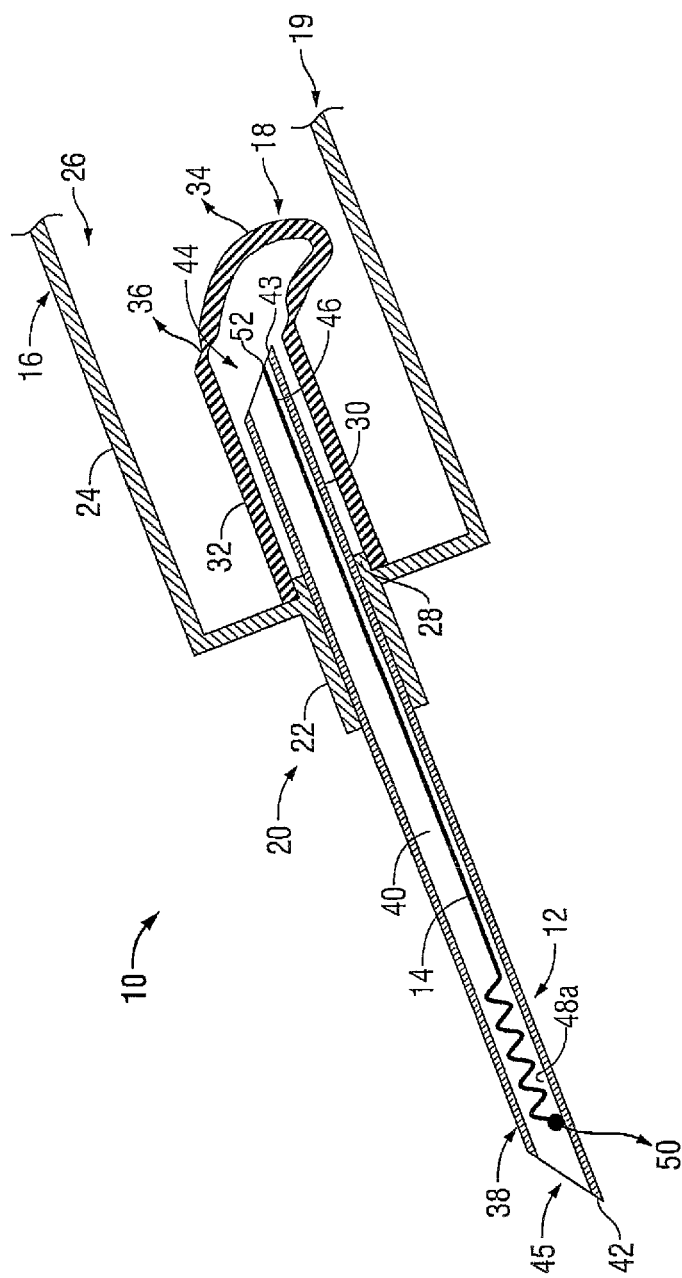
FIG. 1 is a cross-sectional view of an embodiment of the presently disclosed phlebotomy device.

Embodiments of the presently disclosed phlebotomy device will now be described in detail with reference to the drawings wherein like reference numerals designate identical or corresponding elements in each of the several views. In the description that follows, the term "proximal," as is traditional, will refer to the end of the phlebotomy device that is closer to the operator, while the term distal will refer to the end of the device that is farther from the operator.

Figure 2:
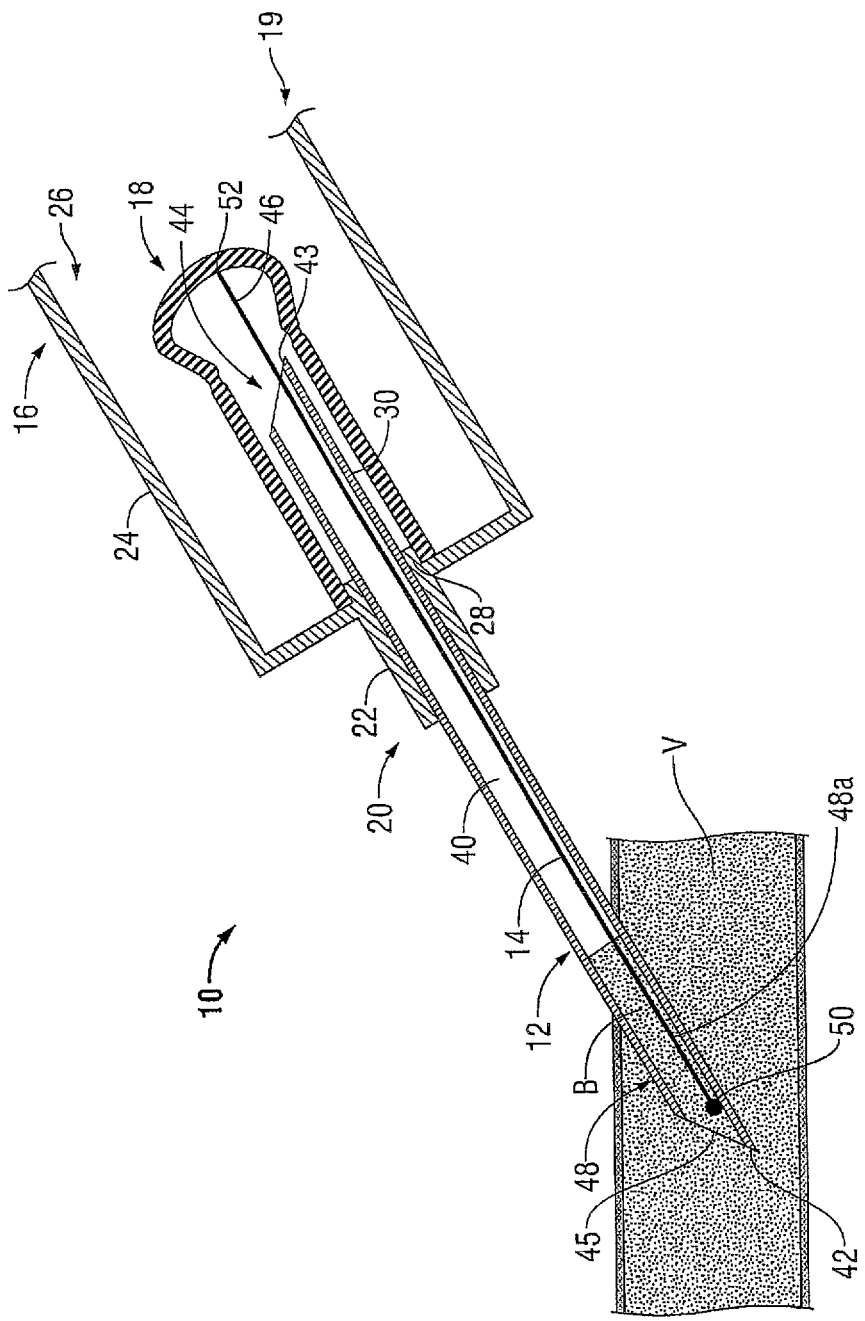
FIG. 2 is a cross-sectional view of the phlebotomy device shown in FIG. 1 inserted into a vein.

FIGS. 1 and 2 illustrate an embodiment of the presently disclosed phlebotomy device 10 adapted to draw blood from a patient. Generally, phlebotomy device 10 includes a needle 12, a sensor 14, and a needle holder 16. Sensor 14 is supported within needle 12. Needle holder 16 supports needle 12 and is configured to receive a blood collection tube (not shown).

Needle holder 16 includes a body 24. Although the drawings show a body 24 having a cylindrical shape, the present disclosure envisions bodies with other configurations. Body 24 defines a cavity 26 adapted to receive a blood collection tube (not shown). In addition, body 24 includes proximal and distal ends 19, 20. Proximal end 19 has an opening adapted to receive a blood collection tube (not shown) and distal end 20 of body 24 is operatively coupled to a portion of needle 12. In one embodiment, distal end 20 includes an engagement portion 22 to facilitate connection of needle 12 to needle holder 16. Engagement portion 22 may include a female fitting configured to engage a male fitting on needle 12. Alternatively, engagement portion 22 may include other engagement structures such as screws threads, snap-type connectors, luers or any other suitable connecting structure. In an alternate embodiment, needle 12 is fastened to engagement portion 22 using an adhesive. A coupling section 28 of engagement portion 22 extends proximally into cavity 26 of needle holder 16. Coupling section 28 facilitates connection between needle holder 16 and a deformable valve 18.

As discussed above, deformable valve 18 is operatively connected to coupling section 28 of needle holder 16 such as with adhesives or by welding or by an interference or snap-type fit. Body 24 of needle holder 16 surrounds deformable valve 18. Deformable valve 18 functions to seal and reseal the proximal portion 30 of needle 12 prior to and after removal of a blood collection tube (not shown) from needle holder 16. In particular, deformable valve 18 includes a tubular section 32 surrounding proximal needle portion 30, an indicator 34, and a wall section 36 connecting tubular section 32 and indicator 34. Wall section 36 is weaker than tubular section 32 and indicator 34. In one embodiment, wall section 36 is formed by a thinner cross-section of material in relation to the cross-section of tubular section 32 and indicator 34, as shown in FIG. 1. Indicator 34 is made of an elastomeric material or any other suitable resilient material. In operation, indicator 34 is moved from a first collapsed position (see FIG. 1) to a second extended position (see FIG. 2) by sensor 14 when needle is properly inserted in vasculature V of a patient.

Needle 12 is mounted to engaging portion 22 of needle holder 16. As previously discussed, deformable valve 18 surrounds proximal needle portion 30 of needle 12. Proximal needle portion 30 has a proximal opening 44 and a sharpened proximal tip 43. Sharpened proximal tip 43 is adapted to pierce deformable valve 18 and a stopper of a blood collection tube when the blood collection tube is positioned in needle holder 16. In addition to proximal needle portion 30, needle 12 also has a distal needle portion 38 and defines a lumen 40 extending therethrough. Distal needle portion 38 includes a distal opening 45 and a sharpened distal tip 42 configured to pierce tissue. Distal opening 45 and proximal opening 44 define the ends of lumen 40. At least a portion of needle 12 may be coated with or made from an insulating material such as a polymer or ceramic.

Sensor 14, which may be a wire or any other suitable apparatus, is disposed at least partially within lumen 40 and includes a proximal end portion 46 and a portion 48a. While proximal end portion 46 of sensor 14 has a general elongate configuration, portion 48a has an extended configuration in its natural state. Alternatively, the portion 48a of the sensor 14 may be positioned anywhere along the length of sensor 14. As illustrated in FIG. 1, portion 48a may have a generally wave-like or sinusoidal shape. Other configurations are envisioned including, for example, helical configuration. A distal end 50, or any other portion of sensor 14, may be fixed to the distal needle portion 38 within lumen 40 such as by welding, crimping, adhesives, or the like. Proximal end portion 46 of sensor 14 has a proximal end 52, which is not attached to needle 12. Proximal end 52 of sensor 14 may be blunt or configured to prevent piercing of deformable valve 18. In one embodiment, proximal end 52 of sensor 14 may be resilient. During use, a resilient proximal end 52 of sensor 14 moves distally when a blood collection tube is positioned within cavity 26 of body 24 of needle holder 16, thereby preventing the piercing of deformable valve 18 by sensor 14.

During use, sensor 14 serves as a flashback sensor by transitioning from a first state to a second state upon exposure to blood at physiological temperature. To this end, sensor 14 may be made of a shape memory alloy, such as nickel titanium, or any other suitable material. In the first state, portion 48a of sensor 14 has a contracted configuration and proximal end 52 of sensor 14 is positioned such that indicator 34 is its first collapsed position (FIG. 1). In the depicted embodiment, portion 48a maintains a contracted configuration at about room temperature. When phlebotomy needle 12 is inserted into the vasculature V (FIG. 2) of a patient and sensor 14 contacts blood at about physiological temperature, sensor 14 transitions to a second state and the configuration of portion 48a is modified moving towards proximal needle portion 30. In one embodiment, portion 48a of sensor 14 becomes substantially linear when sensor 14 contacts blood at physiological temperature. Although the drawings show portion 48a of sensor 14 having a substantially linear shape when in contact with blood at about physiological temperature, it envisioned that portion 48a of sensor 14 may have other extended shapes when exposed to blood at about physiological temperature. In the case of a shape memory alloy sensor 14, portion 48a undergoes a phase transformation and attempts to return to its original crystallographic configuration upon contact with blood at physiological temperature. Since the distal end 50 of structure 14 is fixed to distal needle portion 38, the modification of portion 48a causes proximal end 52 of sensor 14 to move in a proximal direction. As proximal end 52 moves proximally, sensor 14 contacts deformable valve 18 and moves indicator 34 of valve 18 to the second extended position, as depicted in FIG. 2. The change in position of indicator 34 of deformable valve 18 signals to the healthcare professional that a vein has been properly accessed. As will be discussed below, the modified shape of portion 48a of sensor 14 is configured to maintain a contracted configuration such as wave-like or helical configuration.

In operation, healthcare professionals employ phlebotomy device 10 to draw blood from a patient. Phlebotomy device 10 is also capable of sensing flashback. Initially, healthcare professionals identify vasculature V, e.g., vein, and place a tourniquet around the area surrounding the identified vasculature V. The skin about the vasculature should then be palpated to determine the size, depth, and direction of the vasculature. The healthcare professional should subsequently clean the skin area around the vasculature V. At this moment, sensor 14 is in the first state. In the first state, portion 48a of sensor 14 has a contracted configuration and proximal end 52 of sensor 14 is positioned such that indicator 34 is its first collapsed position, as seen in FIG. 1.

After preparing the patient for the phlebotomy procedure, the healthcare professional inserts distal needle portion 38 into the vasculature V of the patient to draw blood from the patient. The sharpened tip 42 of distal needle portion 38 pierces the wall of the vein V. At this time, blood B enters lumen 40 through distal opening 45 of needle 12. The blood flows through lumen 40 and contacts sensor 14. Upon exposure to blood at about physiological temperature, sensor 14 transitions to the second state and the configuration of portion 48a is modified. In one embodiment, sensor 14 expands as it transitions to the second state. Since distal end 50 of sensor 14 is fixed within lumen 40, the proximal end 52 of sensor 14 moves proximally. As proximal end 52 moves proximally, sensor 14 contacts deformable valve 18 and moves indicator 34 of deformable valve 18 to the second extended position, as illustrated in FIG. 2. In the second extended position, deformable valve 18 signals to the healthcare professional that flashback has been achieved.

Deformable valve 18 also serves as a seal. Before positioning the blood collection tube within cavity 26 of body 24, deformable valve 18 seals proximal needle portion 30. When the blood collection tube is inserted into cavity 26, proximal needle portion 30 engages a stopper (not shown) of the blood collection tube and pierces through the stopper. Indicator 34 and sensor 14 are compressed downwardly as proximal needle portion 30 pierces the stopper of the blood collection tube and enters a cavity inside the blood collection tube. The blood collection tube is maintained at a vacuum such that when distal needle portion 38 is properly positioned in the vasculature V of the patient and the blood collection tube is positioned within cavity 26, blood flows through lumen 40 of needle 12 into the blood collection tube. When the blood collection tube is removed from needle holder 16, sensor 14 and indicator 34, which are resilient, return to their second state configuration and deformable valve 18 covers proximal needle portion 30 to seal proximal opening 44 of needle 12.

It will be understood that various modifications may be made to the embodiments disclosed herein. For example, portion 48a of sensor 14 may have a sinusoidal wave or helical configuration in its natural state. In addition, needle holder 16 may include flanges at its proximal end to facilitate handling of phlebotomy device 10. Therefore, the above description should not be construed as limiting, but merely as exemplifications of the embodiments. Those skilled in the art will envision other modifications within the scope and spirit of the claims appended hereto.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A phlebotomy device comprising:
   a needle having a proximal end, a sharp distal end opposite the proximal end, and a lumen extending between the proximal end and the distal end; and
   an elongate sensor positioned at least partially in the lumen and connected to the needle, the sensor having a proximal end free from direct connection to the proximal end of the needle, a distal end opposite the proximal end, a first length measured between the proximal end and the distal end when the sensor is at a first temperature, and a second length longer than said first length when the sensor is at a second temperature higher than said first temperature so that the proximal end of the sensor moves to a more proximal position when subjected to said second temperature than when subjected to said first temperature.

2. A phlebotomy device as set forth in claim 1 wherein the distal end of the sensor is connected directly to the lumen.

3. A phlebotomy device as set forth in claim 1 wherein the sensor comprises a curved portion.

4. A phlebotomy device as set forth in claim 3 wherein the curved portion is sinusoidal.

5. A phlebotomy device as set forth in claim 1 wherein the sensor comprises a shape memory alloy.

6. A phlebotomy device as set forth in claim 1 wherein said second temperature comprises a physiological temperature.

7. A phlebotomy device as set forth in claim 1 wherein the sensor comprises a wire.

8. A phlebotomy device as set forth in claim 1 further comprising a needle holder supporting the needle and having a hollow cavity, the proximal end of the sensor extending into the hollow cavity of the needle holder when the sensor is subjected to said second temperature.

* * * * *